(12) United States Patent
Sanborn et al.

(10) Patent No.: US 10,176,295 B2
(45) Date of Patent: Jan. 8, 2019

(54) SYSTEMS, METHODS, AND COMPOSITIONS FOR VIRAL-ASSOCIATED TUMORS

(71) Applicants: Five3 Genomics, LLC, Santa Cruz, CA (US); Nant Holdings IP, LLC, Culver City, CA (US)

(72) Inventors: John Zachary Sanborn, Santa Cruz, CA (US); Charles Joseph Vaske, Santa Cruz, CA (US); Stephen Charles Benz, Santa Cruz, CA (US); Shahrooz Rabizadeh, Los Angeles, CA (US); Nicole Hensley, Culver City, CA (US); Patrick Soon-Shiong, Los Angeles, CA (US)

(73) Assignees: Five3 Genomics, LLC, Santa Cruz, CA (US); Nant Holdings IP, LLC, Culver City, CA (US)

( * ) Notice: Subject to any disclaimer, the term of this patent is extended or adjusted under 35 U.S.C. 154(b) by 814 days.

(21) Appl. No.: 14/499,023

(22) Filed: Sep. 26, 2014

(65) Prior Publication Data
US 2015/0088432 A1    Mar. 26, 2015

Related U.S. Application Data

(60) Provisional application No. 61/883,153, filed on Sep. 26, 2013.

(51) Int. Cl.
*G06F 19/22* (2011.01)

(52) U.S. Cl.
CPC .................... *G06F 19/22* (2013.01)

(58) Field of Classification Search
CPC ............ C12Q 2600/158; C12Q 1/6886; C12Q 2600/118; C12Q 1/6883; C12Q 1/70; C12Q 2525/179; C12N 7/00; C12N 2740/15043; C12N 15/90; G06F 19/12; G06F 19/3431; G06F 19/22; G06F 19/3487; G06F 17/241; G06F 19/18; G06F 19/28; G06F 19/345; G06F 19/322; G01N 33/574; G01N 33/56983; G16H 50/20; G16H 10/60; G16H 50/30; G06N 7/005; G06Q 50/24
See application file for complete search history.

(56) References Cited

U.S. PATENT DOCUMENTS

| | | | |
|---|---|---|---|
| 8,715,926 B2 | 5/2014 | Duerksen-Hughes et al. | |
| 9,322,067 B2 * | 4/2016 | Von Hoff | C12Q 1/6886 |
| 2005/0048467 A1 | 3/2005 | Sastry et al. | |
| 2006/0160188 A1 | 7/2006 | Kurnit et al. | |
| 2009/0215036 A1 * | 8/2009 | Stropp | C12Q 1/6886 435/6.16 |
| 2009/0258928 A1 | 10/2009 | Beaudenon-Huibregtse et al. | |
| 2011/0229876 A1 * | 9/2011 | Duerksen-Hughes | C12Q 1/6886 435/5 |
| 2012/0059670 A1 * | 3/2012 | Sanborn | G06F 19/22 705/3 |
| 2013/0196308 A1 | 8/2013 | Reijans et al. | |
| 2014/0194317 A1 | 7/2014 | Duerksen-Highes et al. | |

FOREIGN PATENT DOCUMENTS

| | | |
|---|---|---|
| EP | 2708606 A1 | 3/2014 |
| WO | 0153536 A1 | 7/2001 |
| WO | 2009126726 A1 | 10/2009 |
| WO | 2011031982 | 3/2011 |
| WO | 2011038403 A1 | 3/2011 |
| WO | 2014092647 A1 | 6/2014 |

OTHER PUBLICATIONS

Lazo, Pedro A., "Amplification of the Integrated Viral Transforming Genes of Human Papillomavirus 18 and Its 5'—Flanking Cellular Sequence Located Near the myc Protooncogene in HeLa Cells", Journal of American Association for Cancer Research, 1989, vol. 49, pp. 4305-4310, aacrjournals.org.
Mclaughlin-Drubin, Margaret E., et al., "Viruses Associated with Human Cancer", NIH Public Access Author Manuscript, Biochim Biophys Acta. Mar. 1, 2009, vol. 1782(3), pp. 127-150.
Beger, M., et al., "Expression Pattern Of Ap-2 Transcription Factors In Cervical Cancer Cells And Analysis Of Their Influence On Human Papilloma Virus Oncogene Transcription," J. Mol. Med (Berl), Jun. 2001, vol. 79 (5-6): pp. 314-320 (abstract only).
Das, P., et al.,"HPV Genotyping and Site of Viral Integration in Cervical Cancers in Indian Women." PLoS ONE 7(7): e41012. doi:10.1371/journal.pone.0041012 (2012).
Lee, C.M., et al., "Expression of HER2neu (c-erbB-2) and epiderman growth factor receptor in cervical cancer: prognostic correlation with clinical characteristics, and comparison of manual and automated imaging analysis." Gynecologic Oncology 93 (2004) 209-214.
ISA/KR, International Search Report and Written Opinion, Int'l Appln No. PCT/US2014/057859, dated Jan. 2, 2015 (13 pages).
Peter et al., "Frequent genomic structural alterations at HPV insertion sites in cervical carcinoma", Journal of Pathology, vol. 221, pp. 320-330 (2010).
Xu et al., "Multiplex identification of human papillomavirus 16 DNA integration sites in cervical carcinomas", PLoS ONE, vol. 8, Issue 6, Article e66693 (Jun. 18, 2013).
Zhang et a., "Genetic Alterations in Cervical Carcinomas: Frequent Low-Level Amplifications of Oncogenes are Associated with Human Papillomavirus Infection", International Journal of Cancer, John Wiley & Sons Inc, US, vol. 101, No. 5, Oct. 10, 2002, pp. 427-433.

(Continued)

*Primary Examiner* — Mary K Zeman
(74) *Attorney, Agent, or Firm* — Umberg Zipser LLP

(57) ABSTRACT

Contemplated systems and methods employ chimeric reference sequences that include a plurality of viral genome sequences to identify/quantify integration and co-amplification events. Most typically, the viral genome sequences are organized in the chimeric reference sequences as single chromosomes and the chimeric reference sequences are in BAM format.

25 Claims, 3 Drawing Sheets

(56) References Cited

OTHER PUBLICATIONS

Office Action dated Oct. 26, 2017, in Korean Patent Application 10-2016-7010955.
Zhang et al., "Genetic Alterations in Cervical Carcinomas: Frequent Low-Level Amplifications of Oncogenes are Associated with Human Papillomavirus Infection", International Journal of Cancer, John Wiley & Sons Inc, US, vol. 101, No. 5, Oct. 10, 2002, pp. 427-433.
Supplementary European Search Report dated May 2, 2017, in European Patent Application 14847881.1.

* cited by examiner

SYSTEMS, METHODS, AND COMPOSITIONS FOR VIRAL-ASSOCIATED TUMORS

This application claims priority to U.S. provisional application with the Ser. No. 61/883153, which was filed Sep. 26, 2013 and which is incorporated by reference herein.

FIELD OF THE INVENTION

The field of the invention is computational analysis of genetic information from tissue specimen and viral genomes, and especially of viral associated tumors and tumor associated viruses.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

Cervical cancer is the third most common cancer in women worldwide, responsible for approximately 530,000 diagnosed cases and 275,000 deaths a year as of 2008. Due to the origins of most cervical cancers, it is widely considered to be a preventable disease. In the United States alone from 2004-2008, there was an average of 11,967 cases of cervical cancer, 11,500 of which were attributable to HPV infection (Gillison M L, et al. *Cancer.* 2008; 113: 3036-3046). All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply Immunizations (Gardasil and Cervarix) against the most carcinogenic strains of HPV are becoming more available, in addition to Pap smears, which provide for early diagnosis and therefore better treatment outcome.

There are more than 120 Human Papilloma Virus (HPV) subtypes known today; these subtypes are further categorized into low-risk and high risk types. There are currently 15 high-risk types of which HPV 16, 18, 45, 31, 33, 52, and 58 are most prevalent. More than 70% of high-grade intraepithelial neoplasias and invasive cervical carcinomas are either HPV 16+ or HPV 18+ (Schiller J T, et al. *Gynecol Oncol.* 2010 June; 118(1 Suppl): S12-17). In one study over the course of 12 months, 75% of women were able to spontaneously clear their high-risk HPV infection, and over an additional 6 months another 22% were able to clear the infection on their own (Steben, M. et al. *Gynecologic Oncology* 107 (2): S2-S5). However, those who fail to clear the infection on their own (e.g., due to immune compromised status or unknown cause) often develop cervical cancer. While new infections can be prevented via vaccines (e.g., Gardasil and Cervarix), they are ineffective for already infected patients. The current standard of treatment for patients that develop cervical cancer is a cisplatin-based chemoradiation, which fails to cure at least 15% to 45% of bulky stage IB to IIIB patients (Dueñas-Gonzalez A, et al. *Cancer Treat Rev* 2003, 29:389-399). Unfortunately, there are no new and more efficacious treatments on the market for HPV.

Notably, HPV is known to integrate its DNA into a host genome and preferential sites of HPV integration have been reported (e.g., Popescu et al. *Cancer Genet Cytogenet* 42: 157-171. 1989). As was reported elsewhere, HPV has been shown to integrate next to the N-Myc gene (2p24) and c-Myc gene (8q24. 1) (Couturier et al., *J Virol* 65: 4534-4538. 1991), which can result in deregulated expression of Myc proteins. Co-amplification of HPV and c-Myc has also been observed in a newly established cervical carcinoma line (Gotoh et al., *Jpn. J. Cancer Res.* 82: 1252-1257. 1991). In further studies, c-Myc protein levels in cervical biopsies were determined by quantitative fluorescent immunohistochemistry, and the data suggested that c-Myc protein levels play a role in early and late cervical lesions. Prolonged overexpression of c-Myc in early lesions is thought to allow for stable amplification of DHFR, which shows increased gene amplification over time and remains an indicator of tumor progression. In other reports, expression of oncoproteins E6 and E7 in high-risk types of HPV were thought to inactivate TP53 and RB1, respectively, and thus take control of both cell cycle and apoptosis, while MDM2 was upregulated in squamous intraepithelial lesions (Arvanitis et al., *Oncol Rep.* 2008 October; 20(4):751-60).

Less prevalent in cervical cancer, yet more treatment-relevant, is the amplification or over-expression of ERBB2 (Erythroblastic Leukemia Viral Oncogene Homolog 2), known more commonly as HER2/neu. ERBB2 is a proto-oncogene located on chromosome 17q12. Over-expression of ERBB2 has most commonly been linked to aggressive breast cancer, but in recent years has begun gaining traction as a biomarker for other cancers. ERBB2 has in most cases a relatively low expression in cervical cancers, and widely varying results place the range of ERBB2 expression in cervical carcinomas from 1%-42% (Rosty C, et al. *Int J Gynecol Pathol* 2004; 23:13-7), depending on both the study site and severity of cancer. Regardless of pervasiveness, ERBB2 expression is associated with some of the most aggressive types of cancer often resulting in poor survival rates (Berchuck A. et al. *Cancer Res.* 1990 Jul. 1; 50(13): 4087-91), and rarity of cervical adenocarcinomas which overexpress ERBB2 were described elsewhere (Fadare, et al. *International Journal of Gynecological Pathology* Volume 23, Issue 4 Oct. 2004). Treatment with cervical cancer patients with humanized monoclonal antibody trastuzumab is currently under review in ERBB2+ cervical cancer patients.

Therefore, while numerous treatment options for various cancers are available, and while molecular characterization of patients' and pathogens' genomes have become more and more routine, there is still a need for a better understanding in molecular events occurring in both, the pathogen's and the patient's genome in viral associated diseases and especially viral associated cervical cancer to help tailor therapies to an individual's disease.

SUMMARY OF THE INVENTION

The inventive subject matter is directed to systems, methods, and devices for viral-associated tumors that help better understand interactions between and/or changes in the genome of a pathogen and a patient. Among other things, identification and characterization of interactions that are indicative of genomic exchange are particularly contemplated, which may provide unique treatment options based on the specific type of genomic exchange.

For example, in one aspect of the inventive subject matter, a method is contemplated that includes a step of informationally coupling an analysis engine to a sequence database that stores a nucleic acid sequence from a virus-associated tumor and a chimeric reference nucleic acid sequence. Most typically, the chimeric reference nucleic acid sequence comprises one or more viral nucleic acid sequences together with a mammalian nucleic acid sequence. In another step of contemplated methods, the analysis engine is used to identify integration of at least some of the viral nucleic acid sequence in the chimeric reference nucleic acid sequence with an allele (e.g., oncogene) in the nucleic acid sequence from the virus-associated tumor. In a still further step, the analysis engine is used to identify co-amplification of the allele and the viral nucleic acid sequence(s), and in yet another step, a treatment recommendation record is updated for the virus-associated tumor once co-amplification reaches a threshold value (e.g., greater than 10 amplifications).

With respect to the nucleic acid sequence from the virus-associated tumor it is contemplated that such sequence includes at least nucleic acid sequences of one or more chromosomes of the virus-associated tumor, at least 50% of an exome of the virus-associated tumor, and/or at least 50% of the entire genome of the virus-associated tumor.

In further contemplated aspects, the virus-associated tumor is associated with HTLV-1 (Human T-Cell Leukemia Virus), an HPV virus (Human Papillomavirus), HHV-8 (Human Herpes Virus 8), EBV (Epstein-Barr Virus), HBV (Hepatitis B Virus), HCV (Hepatitis C Virus), SV40 (Simian Vacuolating Virus 40), BKV (BK virus), JCV (JC virus), a HERV (human endogenous retrovirus), HMTV (human mammary tumor virus), KSHV (Kaposi's Sarcoma-Associated Herpesvirus), and/or TTV (Torque teno virus). Of course, where such viruses have distinct risk type, genotypes and/or serotypes, further sub-classifications are also considered. For example, the virus-associated tumor may be associated with a high-risk HPV virus of type 16, 18, 31, 33, 35, 39, 45, 51, 52, 56, 58, 59, 68, 69, 73, or 82. Therefore, it is contemplated that the chimeric reference nucleic acid sequence may include a plurality of viral nucleic acid sequences from a plurality of distinct viruses.

Most typically, but not necessarily, the mammalian nucleic acid sequence in the chimeric reference nucleic acid sequence is a matched normal mammalian nucleic acid sequence. It is further preferred that the nucleic acid sequence from the virus-associated tumor and the chimeric reference nucleic acid sequence are in BAM/SAM/FASTA or FASTA index format.

In other aspects of the inventive subject matter, it is contemplated that the step of identifying the integration includes an identification of a location of integration, and contemplated methods may further include a step of determining a solution for a genomic arrangement comprising the co-amplified sequences (e.g., circular or tandem repeat).

Therefore, viewed from a different perspective, the inventors also contemplate a method in which an analysis engine is informationally coupled to a sequence database that stores nucleic acid sequence(s) from mammalian tissue(s) and chimeric reference nucleic acid sequence(s). Most typically, the chimeric reference nucleic acid sequence includes at least one viral nucleic acid sequence and optionally a mammalian nucleic acid sequence. In another step, an analysis engine identifies an integration of at least some of the nucleic acid sequence from the mammalian tissue into the viral nucleic acid sequence, as well as co-amplification of an allele (e.g., oncogene) of the nucleic acid sequence from the mammalian tissue and at least some of the viral nucleic acid sequence. In yet another step, a treatment recommendation record for the mammal is updated once co-amplification reaches a threshold value (e.g., greater than 10 amplifications).

Most typically, the chimeric tissue will be a diseased tissue, and most typically a neoplastic cancerous tissue (e.g., tumor tissue of a virus-associated tumor). It is also contemplated that the nucleic acid sequence from the mammalian tissue comprises at least nucleic acid sequences of one chromosome of the mammalian tissue, at least 50% of an exome of the mammalian tissue, and/or at least 50% of an entire genome of the mammalian tissue.

Similarly, it is typically preferred that the chimeric reference nucleic acid sequence comprises a nucleic acid sequences of a plurality of distinct viruses, and most typically a nucleic acid sequence of one or more tumor associated viruses. For example, contemplated tumor associated viruses include HTLV-1 (Human T-Cell Leukemia Virus), an HPV virus (Human Papillomavirus), HHV-8 (Human Herpes Virus 8), EBV (Epstein-Barr Virus), HBV (Hepatitis B Virus), HCV (Hepatitis C Virus), SV40 (Simian Vacuolating Virus 40), BKV (BK virus), JCV (JC virus), a HERV (human endogenous retrovirus), HMTV (human mammary tumor virus), KSHV (Kaposi's Sarcoma-Associated Herpesvirus), and TTV (Torque teno virus). Such viruses may be further subclassified as already noted above. For example, tumor associated virus may be high-risk HPV viruses of type 16, 18, 31, 33, 35, 39, 45, 51, 52, 56, 58, 59, 68, 69, 73, or 82. While not limiting to the inventive subject matter of such methods, it is generally preferred that the chimeric reference nucleic acid sequence comprises the mammalian nucleic acid sequence.

In yet other aspects of the inventive subject matter, the mammalian nucleic acid sequence is a matched normal mammalian nucleic acid sequence, and it is generally contemplated that the methods presented herein may include a step of determining a solution (e.g., circular solution or a tandem duplication) for a genomic arrangement that includes the co-amplified sequences.

Consequently, the inventors also contemplate a method that includes a step of informationally coupling an analysis engine to a sequence database that stores a nucleic acid sequence from a cervical tumor of a patient and a chimeric reference nucleic acid sequence. As noted before, it is generally preferred in such methods that the chimeric reference nucleic acid sequence comprises a matched normal nucleic acid sequence from the patient and a viral nucleic acid sequence of an HPV virus. In a further step of contemplated methods, an analysis engine is used to identify an integration of at least some of the viral nucleic acid sequence in the chimeric reference nucleic acid sequence with an allele of an oncogene in the nucleic acid sequence from the cervical tumor, and the analysis engine is further used to, identify co-amplification of the allele and the viral nucleic acid sequence(s). Upon reaching a predetermined threshold value, a treatment recommendation record for the virus-associated tumor is then updated or generated (e.g., administration of a drug targeting the oncogene).

In one typical aspect of contemplated methods, the nucleic acid sequence from the cervical tumor includes at least nucleic acid sequences of one chromosome of the cervical tumor, at least 50% of an exome of the cervical tumor, and/or at least 50% of an entire genome of the cervical tumor. Furthermore, with respect to the chimeric reference nucleic acid sequence it is contemplated that such sequence comprises at least two nucleic acid sequences of an HPV virus of type 16, 18, 31, 33, 35, 39, 45, 51, 52, 56, 58, 59, 68, 69, 73, and 82. Such sequences preferably cover the entire genome of the HPV virus.

In further contemplated aspects, the oncogene may be a gene encoding a growth factor receptor, and especially ERBB2, and it is further contemplated that the allele is a homozygous allele. As noted above, it is also contemplated that such methods further comprise a step of determining a solution (e.g., circular solution or a tandem duplication) for a genomic arrangement comprising the co-amplified sequences.

In yet further aspects of the inventive subject matter, a method is contemplated that comprises a step of informationally coupling an editing engine to a sequence database that stores a nucleic acid sequence from a mammalian tissue (e.g., matched normal sequence for the mammal) and a plurality of viral nucleic acid sequences from a plurality of distinct viruses. The editing engine is then used to merge the nucleic acid sequence from the mammalian tissue with the plurality of viral nucleic acid sequences into a single chimeric nucleic acid sequence file, wherein the nucleic acid sequence from the mammalian tissue is organized in the single chimeric nucleic acid sequence file following a chromosomal structure, and wherein each of the plurality of viral nucleic acid sequences is organized in the single chimeric nucleic acid sequence file as a single chromosome. In a further step of contemplated methods, the sequence database is then updated with the single chimeric genomic file.

As noted above, it is contemplated that the nucleic acid sequence from the mammalian tissue comprises at least nucleic acid sequences of one chromosome of the mammalian tissue, at least 50% of an exome of the mammalian tissue, and/or at least 50% of an entire genome of the mammalian tissue. Moreover, it is contemplated that the distinct viruses are tumor-associated viruses, which may include HTLV-1 (Human T-Cell Leukemia Virus), an HPV virus (Human Papillomavirus), HHV-8 (Human Herpes Virus 8), EBV (Epstein-Barr Virus), HBV (Hepatitis B Virus), HCV (Hepatitis C Virus), SV40 (Simian Vacuolating Virus 40), BKV (BK virus), JCV (JC virus), a HERV (human endogenous retrovirus), HMTV (human mammary tumor virus), KSHV (Kaposi's Sarcoma-Associated Herpesvirus), and TTV (Torque teno virus). Where the virus is an HPV virus, especially contemplated viruses include an HPV virus of type 16, 18, 31, 33, 35, 39, 45, 51, 52, 56, 58, 59, 68, 69, 73, or 82.

While not limiting to the inventive subject matter, it is generally preferred that the step of merging comprises appending to the nucleic acid sequence from the mammalian tissue the plurality of viral nucleic acid sequences, and/or that at least one (and most typically all) of the nucleic acid sequence from the mammalian tissue, the plurality of viral nucleic acid sequences, and the single chimeric nucleic acid sequence file is in BAM/SAM/FASTA or FASTA index format.

Various objects, features, aspects and advantages of the inventive subject matter will become more apparent from the following detailed description of preferred embodiments, along with the accompanying drawing in which like numerals represent like components.

DETAILED DESCRIPTION

Figure 1:
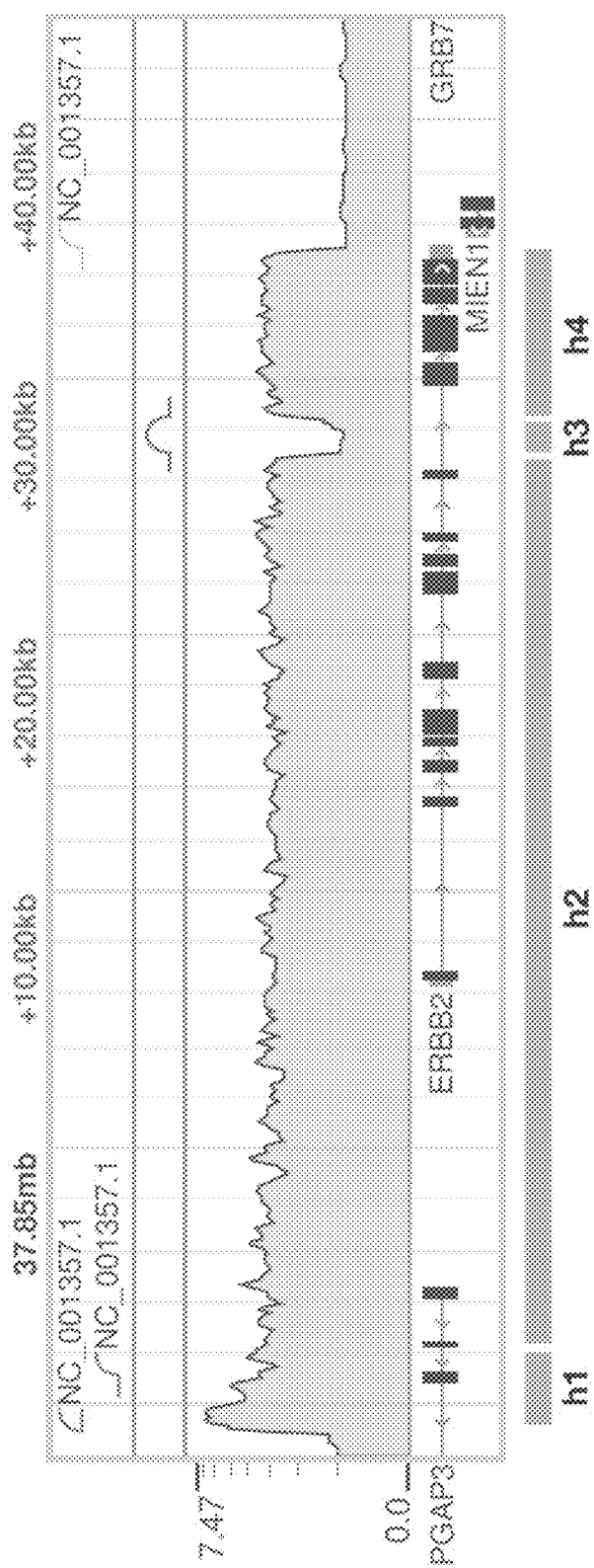
FIG. 1 is a detail view of an exemplary result of a tumor DNA analysis in which integration and co-amplification of tumor-associated HPV-18 DNA (NC_001357.1) into human chromosome 17 is depicted. Only a portion of chromosome 17 is depicted.

The inventors have discovered that certain tumors can be hosts to viral nucleic acids, especially where the tumors are known to be associated with a prior viral infection (i.e., viral-associated tumors). Conversely, the inventors have also discovered that the virus can acquire portions of the host genome. Once acquired, the inventors further discovered that the tumor associated viral nucleic acid sequences and the host nucleic acid sequences are co-amplified during viral replication. Where the replicated viral nucleic acid includes an oncogene from the host, co-amplification can present adverse consequences but also new treatment options for the host. Consequently, the inventors contemplate that diagnosis, therapy, and other treatment options can be informed by genome analysis of the patient and/or a virus sample from the patient in which analysis includes identification of (typically mutual) exchange and/or co-amplification of genomic content.

For example, and as discussed in more detail below, the inventors discovered through genomic analysis of a patient sample of a poorly differentiated adenocarcinoma of the cervix genomic exchange/fusion between the patient genome and the viral genome of an HPV-18 virus. While integration of HPV-18 into a host genome was previously reported, and while it was previously suggested that cancer in the host was attributed to the regulatory influence of viral E6/E7 genes on the host genome, the inventors now discovered an entirely different potential mode of action. More specifically, the inventors discovered that viral integration of HPV with the host genome was accompanied by substantial co-amplification of an oncogene of the host (here: ERBB2 gene) and large portions of the viral genome. As used herein, the term "co-amplification" of a first and second gene refers to an amplification of both the first and the second gene in the same copy number. In most cases, and as also further discussed in more detail below, it was observed that co-amplification was only with respect to a single allele. Such genomic fusions may be present as integration of viral sequences with the patient genome (typically as tandem repeats) and/or as extrachromosomal structures (e.g., as circular viral genome) or even virus particles. However, for example, where co-amplification occurs after independent amplification of a first allele, the result of co-amplification may also be asymmetric with respect to the copy numbers of first and second alleles.

Therefore, where the co-amplified host nucleic acid comprises an oncogene, a tumor suppressor gene, a gene involved in cell cycle regulation, and/or a gene involved in division of a cell, detection of virally associated amplification of such host nucleic acid (e.g., ERBB2) may influence/guide drug treatment of a virally associated tumor with drugs targeting that host nucleic acid. Viewed from another perspective, it should be appreciated that targeting the function of amplified host nucleic acids may serve as a new mode of treatment of virally associated tumors.

It should be particularly appreciated that contemplated systems and methods will be especially advantageous where a patient is diagnosed or suspected to have a virus-associated cancer. As in such patient population knowledge of a potential interaction between the viral and host genome may critically inform treatment options, systems and methods contemplated herein will be based on rapid identification and characterization of genomic integration viral and host genomic sequences and/or co-amplification viral and host genomic sequences. The inventors have now discovered that such rapid analysis can be achieved by modification of a reference genome (which may be obtained from healthy host tissue or from a non-host tissue) in silico where one or more viral genome sequences (and most preferably the entire viral genome) is merged with the reference genome to so form a chimeric reference nucleic acid sequence.

Suitable reference genomes for use in the chimeric reference nucleic acid sequence include whole genome nucleic acid sequences of the same patient and are typically obtained from non-diseased tissue. For example, a reference genome nucleic acid may be obtained from whole blood, from tissue adjacent to a cancerous tissue, or from a buccal swab or biopsy. Alternatively, the reference genome may also be obtained from a sample taken earlier from the patient, or a previous whole genome sequencing attempt. In still further alternative aspects, the reference genome may also be a genome sequence from the same species (e.g., human or other mammalian), preferably stratified by gender, or a average or consensus sequence for the same species. Most typically, the reference genome will be or encompass the entire genome. However, smaller portions of the genome are also contemplated and include at least one chromosome, or two-five chromosomes, or five-ten chromosomes, or more than ten chromosomes. Alternatively, the reference genome may also be only representative of a portion (e.g., between 1-10%, between 10-30%, between 30-60%, or between 60-90%) of the entire exome or entire transcriptome. Thus, and viewed form yet another perspective, the reference genome will typically include at least 10%, or at least 30%, or at least 50%, or at least 70% of the entire genome of the human (or other species).

Suitable viral genomes for use in the chimeric reference nucleic acid sequence include whole genome nucleic acid sequences of at least one virus, and more typically of a collection of viruses with known association with a disease, and especially of tumor-associated viruses (i.e., virus that is known to be associated with a cancerous disease). For example, genome sequences of viruses deemed suitable for use herein include those from HTLV-1 (associated with adult T-cell leukemia), HPV viruses (associated with cervical cancer, skin cancer, head and neck cancer, and anogenital cancers), HHV-8 (associated with Kaposi's sarcoma, primary effusion lymphoma, Castleman's disease), EBV (associated with Burkitt's Lymphoma, nasopharyngeal carcinoma, post-transplant lymphomas, and Hodgkin's disease), HBV and HCV (associated with hepatocellular carcinoma), SV40 (associated with brain cancer, bone cancer, mesothelioma), BKV (associated with prostate cancer), JCV (associated with brain cancer), HERVs (associated with germ cell tumors, breast cancer, ovarian cancer, and melanoma), HMTV (associated with breast cancer), KSHV (associated with Kaposi's Sarcoma), and TTV (associated with gastrointestinal cancer, lung cancer, breast cancer, and myeloma). However, it should be appreciated that suitable viruses also include those that are not currently known for a particular disease association.

On the other hand, virus sequences suitable for use herein may also be stratified by one or more common classifiers, which may include organ specificity (e.g., HBV, HCV), cancer type specificity, or risk-type within a group of viruses. For example, where the virus is an HPV virus, suitable viral genome sequences may include those associated with high-risk for cervical or other urogenital cancer, including HPV type 16, 18, 31, 33, 35, 39, 45, 51, 52, 56, 58, 59, 68, 69, 73, and/or 82. Most typically, the viral genome will be or encompass the entire genome. However, smaller portions of the genome are also contemplated and include portions of the viral genome, for example, one or more single viral genes or transcription units, or at least 10%, or at least 30%, or at least 50%, or at least 70% of the entire genome of the virus.

It is particularly preferred that the chimeric reference nucleic acid sequence will include the viral nucleic acid sequence(s) as one or more individual units that are appended to the reference genome nucleic acid sequence. Most typically, the individual units for the respective viral nucleic acid sequence will be organized/labeled as individual chromosomes. Among other advantages, it should be noted that using such arrangement (particularly where the sequence comparison is done using incremental synchronous alignment) will allow for rapid identification of the location of the genomic integration, copy number determination, and affected alleles. Therefore, it is also contemplated that the viral nucleic acid sequences will be organized in the same format (e.g., BAM, SAM, FASTA, or FASTA index) as the reference genome nucleic acid sequence, however, alternative formats are not expressly excluded. In view of the above, it should thus be recognized that the chromosome count for a chimeric reference nucleic acid sequence for a mammal may significantly exceed the chromosome count for the nucleic acid sequence from the virus-associated tumor. For example, the chromosome count for the chimeric reference nucleic acid sequence may exceed the chromosome count for the nucleic acid sequence from the virus-associated tumor by at least one, at least five, at least ten, at least 20, at least 50, and even more. Indeed, the exact chromosome count will be determined by the number of viral genome sequences to be included.

To that end, the inventors contemplate a method in which a reference sequence for genome analysis is modified by informationally coupling an editing engine to a sequence database that stores one or more nucleic acid sequences from mammalian tissues and one or more viral nucleic acid sequences from respective distinct viruses. The editing engine is then used to merge the nucleic acid sequence(s) from the mammalian tissue with the plurality of viral nucleic acid sequences into a single chimeric nucleic acid sequence file. Of course, it should be appreciated that such editing can be performed manually using a relatively small number of selected viral genomic sequences, or in an automated fashion where the collection of viruses is relatively large. Moreover, it should be appreciated that the editing engine may merge the viral sequences in any format to the (e.g., mammalian/human) reference sequence, and that the viral sequences may be transformed in the desired end format (e.g., BAM, SAM, FASTA, or FASTA index format) at any given time. However, it is generally preferred that the viral sequences are already in the desired end format (e.g., BAM, SAM, FASTA, or FASTA index format). For example, the reference sequence or reference sequences may be stored in a FASTA file with an associated FASTA Index, and that file may then be merged with one or more viral genome sequences as noted above. Further conversion in BAM format can be performed if desired/needed. Furthermore, the sequencing data from the patient's tumor that contain viral sequences may also be stored in the BAM file.

Moreover, with respect to the structure of the chimeric nucleic acid sequence, it is especially preferred that the nucleic acid sequence from the mammalian tissue is organized in the single chimeric nucleic acid sequence file following a chromosomal structure (as is, for example, the case in a BAM format), while the viral nucleic acid sequences are organized in the single chimeric nucleic acid sequence file as respective single chromosomes. Once the chimeric nucleic acid sequence file has been assembled, it is preferred that the sequence database is then updated with the so produced chimeric nucleic acid sequence file. Of course, it should also be recognized that the editing engine may also be employed for on-the-fly merging of the nucleic acid sequence from a mammalian tissue with one or more viral nucleic acid sequences from a library of virus genome sequences such that incremental synchronous alignment can be performed as further discussed below. With respect to suitable sequences and portions thereof, the same considerations as already provided above apply.

With respect to suitable patient samples for comparison with the chimeric nucleic acid sequence it is generally preferred that the patient sample is obtained from a patient diagnosed or suspected to have a cancer, and especially a virus-associated cancer. There are numerous manners of obtaining such samples, and it is generally preferred that the sample includes cancerous tissue. The sample is then processed in well known manners to obtain a nucleic acid sequence from the diseased tissue (e.g., virus-associated tumor). In especially preferred aspects of the inventive subject matter, the coverage of the entire genome is at least 20-fold, and more at least 30-fold. Thus, it is generally preferred that the nucleic acid sequence from the virus-associated tumor will cover the entire genome of the tumor. However, it should also be appreciated that smaller nucleic acid portions of the virus-associated tumor are also deemed suitable, especially where location of an integration event is already suspected. Thus, it is contemplated that the nucleic acid sequence from the virus-associated tumor comprises at least nucleic acid sequences of one chromosome, three chromosomes, five chromosomes, or ten chromosomes of the virus-associated tumor. Viewed from another perspective, it is also contemplated that the nucleic acid sequence from the virus-associated tumor comprises at least a fraction of an exome (e.g., at least 10% or between 10-30%, at least 13% or between 30-50%, at least 50% or between 50-80%) of the virus-associated tumor. Consequently, the nucleic acid sequence from the virus-associated tumor may comprises at least 10% (e.g., between 10-30%, or more), at least 30% (e.g., between 30-50%, or more), at least 50% (e.g., between 50-80%, or more) of an entire genome of the virus-associated tumor.

In that regard, it should be noted that all samples are deemed suitable for use herein that are obtained from a diseased tissue, whether or not such tissue is a cancerous or even precancerous tissue. Indeed, all diseased tissue and tissue suspected to be diseased is deemed appropriate for use herein. However, especially preferred tissues includes those that are obtained from a virus-associated tumor. For example, exemplary viruses for virus-associated tumors include those associated with associated with HTLV-1 (Human T-Cell Leukemia Virus), an HPV virus (Human Papillomavirus, especially high-risk types 16, 18, 31, 33, 35, 39, 45, 51, 52, 56, 58, 59, 68, 69, 73, and/or 82), HHV-8 (Human Herpes Virus 8), EBV (Epstein-Barr Virus), HBV (Hepatitis B Virus), HCV (Hepatitis C Virus), SV40 (Simian Vacuolating Virus 40), BKV (BK virus), JCV (JC virus), a HERV (human endogenous retrovirus), HMTV (human mammary tumor virus), KSHV (Kaposi's Sarcoma-Associated Herpesvirus), and/or TTV (Torque teno virus).

As noted already before, numerous data formats are suitable for use herein, however, especially preferred data formats for the nucleic acid sequence from the virus-associated tumor include BAM, SAM, FASTA, or FASTA index formats. Moreover, it should be noted that the formats for the nucleic acid sequence from the virus-associated tumor and the chimeric reference nucleic acid sequence are the same to allow for rapid incremental synchronous alignment.

In further particularly preferred aspects of the inventive subject matter, the chimeric reference nucleic acid sequence and the nucleic acid sequence from the virus-associated tumor are processed using incremental synchronized alignment to enable rapid identification of integration, co-amplification, and location of genomic exchange. For example, and while not limiting the inventive subject matter, it is generally preferred that the genomic analysis is performed using a software tool in which a chimeric reference nucleic acid sequence (that includes genomic nucleic acid sequence from healthy or reference tissue) is synchronized and incrementally compared against the nucleic acid sequence from the virus-associated tumor (or other diseased tissue). One especially preferred tool includes BAMBAM as previously described in WO2013/074058A1, incorporated by reference herein.

Using such approach, it should be especially appreciated that not only presence of cross-species integrated sequences can be found in the respective samples (e.g., virus and patient), but also the location, copy number, mutations, etc, all of which may have significant impact in terms of disease presence, progression, and/or outcome. Thus, the inventors not only contemplate a method of detecting one or more cross-species integration events, but also a characterization of such events that is then used as a basis for evaluation of treatment and prognosis.

It should also be noted that contemplated analyses need not be limited only to those in which a patient tumor sample is subjected to genomic analysis, but that tests and methods are contemplated in which a patient sample (e.g., blood draw or procurement of other biological fluid (e.g., urine, tear fluid, saliva, spinal fluid, etc.)) is used as is or processed to enrich the sample in viral nucleic acid content. The so obtained sample can then be analyzed to identify the presence of at least a portion of a viral genome where that portion also includes at least a portion of a host genome. Thus, contemplated systems and methods also extend to analyses using incremental synchronized alignment between viral genomic nucleic acid sequences obtained from a sample and a human (or other mammalian) reference genome that may or may not be a chimeric reference nucleic acid sequence as already described above.

Therefore, contemplated systems and methods also include diagnostic tests to confirm or rule out current or prior viral infection with a virus, and especially a tumor-associated virus in the patient. Thus, contemplated diagnostic methods will also include a step of ascertaining that the tumor is associated with a previous (or concurrent) viral infection. Such review for the presence of the virus can be performed via detection of viral antigens, presence of antibodies against viral antigens, molecular biological methods of detecting viral nucleic acids, epitopes, and/or enzymes, etc. Once presence is confirmed or suspected, the selection of appropriate viral genomic sequences may be based on the detected virus (e.g., to select a class or type of virus, including Hepatitis virus, or HPV type).

Regardless of the nature of the particular sequence, it is generally contemplated that the nucleic acid sequences are stored on a database for retrieval by an analysis engine and/or an editing engine, and such database may be a single or a distributed database. Thus, the term 'database' should be understood as not being limited to a single physical device, but to include multiple and distinct storage devices that are informationally coupled to each other. It should further be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Consequently, the inventors contemplate a method in which an analysis engine is informationally coupled to a sequence database that stores a nucleic acid sequence from a virus-associated tumor and a chimeric reference nucleic acid sequence, wherein the chimeric reference nucleic acid sequence comprises at least one viral nucleic acid sequence and a mammalian nucleic acid sequence. The analysis engine is then used to (a) identify integration of at least some of the viral nucleic acid sequence in the chimeric reference nucleic acid sequence with an allele in the nucleic acid sequence from the virus-associated tumor, and (b) identify co-amplification of the allele and the at least some of the viral nucleic acid sequence. Upon completion of the analysis, a treatment recommendation record for the virus-associated tumor is then updated once co-amplification reaches a threshold value (e.g., threshold is at least 2-fold amplification, at least 3-fold amplification, at least 5-fold amplification, or at least 10-fold amplification, higher). Most typically, such record will be in electronic form and may be stored on any device that is informationally coupled to the analysis engine (e.g., mobile device of a patient or medical professional, local server of a medical practice or healthcare provider, etc.)

Viewed form a different perspective, the inventors also contemplate a method in which an analysis engine is informationally coupled to a sequence database storing a nucleic acid sequence from a mammalian tissue and a chimeric reference nucleic acid sequence. In such methods, the chimeric reference nucleic acid sequence will include at least one viral nucleic acid sequence (more typically at least two, at least five, at least 10, and more) and may also further include a mammalian (e.g., human) nucleic acid sequence. The analysis engine is then used to identify integration of at least some of the nucleic acid sequence from the mammalian tissue into the viral nucleic acid sequence, and further used to identify a co-amplification of an allele of the nucleic acid sequence from the mammalian tissue and at least some of the viral nucleic acid sequence. As before, a treatment recommendation record for the mammal is then updated once co-amplification reaches a threshold value, and such record will be in electronic form and may be stored on any device that is informationally coupled to the analysis engine.

Likewise, and with further respect to the example below, the inventors contemplate a method in which an analysis engine is informationally coupled to a sequence database storing a nucleic acid sequence from a cervical tumor of a patient and a chimeric reference nucleic acid sequence, wherein the chimeric reference nucleic acid sequence comprises a reference sequence (preferably a matched normal nucleic acid sequence) from the patient and one or more viral nucleic acid sequences of an HPV virus. An analysis engine is then used to identify an integration of at least some of the viral nucleic acid sequence in the chimeric reference nucleic acid sequence with at least one allele of an oncogene (e.g., gene encoding a growth factor receptor, including ERBB2, or a tumor suppressor gene, a gene involved in cell cycle regulation, and/or a gene involved in division of a cell) in the nucleic acid sequence from the cervical tumor. In another step, the analysis engine is also used to identify a co-amplification of the allele and the at least some of the viral nucleic acid sequence, and a treatment recommendation record for the virus-associated tumor is updated once the co-amplification reaches a threshold value.

It should be recognized that synchronized incremental analysis and enormous size of sequence files will render such method entirely unsuitable for human practice as such file analysis would readily exceed the lifespan of a human, even if one would analyze 10,000s of bases per day. Moreover, calculation of solutions for genomic arrangements will further add to the impossibility of human action. In addition, it should be pointed out that the particular file structure of the chimeric reference nucleic acid (i.e., merged viral nucleic acid sequence and mammalian nucleic acid sequence, with viral sequences organized/indexed as individual chromosomes) will have the technical effect of drastically improving analysis time as such file structure (a) can be rapidly processed without much memory demand as compared to loading an entire sequence into memory, and (b) allows for rapid analysis of genomic integration and identification of co-amplification as such method requires only analysis of two sequence files rather than three or more as otherwise dictated by the number of viruses.

Moreover, all methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In yet further contemplated methods, it should be recognized that upon identification of the co-amplification of a gene from the host of the virus (e.g., oncogene, tumor suppressor gene, gene involved in cell cycle regulation, and/or a gene involved in division of a cell), the so obtained result may be used to model in silico a potential impact of the amplified portion of the host genome to thereby identify additional treatment options and targets. Among other modeling systems, especially preferred modeling systems include pathway analysis models and particularly PARADIGM, which is described in WO2011/139345 and WO/2013/062505, both of which are incorporated by reference herein. For example, where it is discovered that ERBB2 is amplified, such information can be used in the pathway recognition algorithm to investigate treatment methods other than or in addition to inhibition of the gene product of ERBB2.

EXAMPLE

Patient History: A 44-year-old female was found to have a cervical polyp in March, 2012. The polyp was biopsied and found to be a poorly differentiated adenocarcinoma of the cervix. Her prior pap smears had all been normal, the last one done in September, 2011. In April, 2012, she underwent a radical hysterectomy, including bilateral salpingectomy and lymphadenectomy. The patient chose to preserve her ovaries. The surgical pathology demonstrated wall invasion to outer third of the cervix. Horizontal spread was to 2.7 cm. There was no lymphatic, vascular, or parametrial invasion seen. Lymph nodes were negative. The patient did not receive any post-op chemotherapy or radiation therapy. Her post-op course was complicated by pelvic abscesses and sepsis from which she recovered. She was able to return to work within 8 weeks and was otherwise normal.

In July, 2012, the patient developed pelvic discomfort and dysuria. A work-up, which included ultrasound, CT scan, and PET scan, showed multiple pelvic masses with a maximal SUV of 43.9. A needle biopsy confirmed a poorly differentiated adenocarcinoma, consistent with the original biopsy. The patient was begun on carboplatin and gemcitabine but was switched to vinorelbine, tamoxifen, and gefitinib in August, 2012 because of in vitro testing results performed elsewhere. After 4 weekly doses, the tumor was found to be progressing on repeat CT/PET, and the patient was switched back to carboplatin and gemcitabine and received one dose. The patient then elected to undergo "alternative therapies". The disease continued to progress, and in late September, 2012 developed obstructive renal failure, which was treated with ureteral stents.

In late November, 2012, the patient underwent laparoscopic biopsy of her metastatic tumor to be used for a variety of tests, including whole genome sequencing; cancer gene panel sequencing; RNA expression profiling, immunohistology, and FISH, and xenografting into immunodeficient mice. These tests all confirmed that the HER2 (ERBB2) gene was amplified and the protein overexpressed. In December, 2012, the patient was treated with trastuzumab and lapatinib with an excellent response. Her abdominal pain resolved; she lost 30 pounds of ascites fluid, and her left lower extremity lymphedema all resolved within three weeks. The CT/PET scan in February, 2013 confirmed the significant response of her tumor.

The patient did well until April, 2013, when she developed dyspnea on exertion and pain. A CT/PET scan showed disease progression with pleural effusions and severe hydronephrosis. Nephrostomy tubes were placed. The trastuzumab was stopped and she was started on ado-trastuzumab emtansine q3wks as well a pertuzumab along with the lapatinib. The repeat CT/PET scan in June, 2013 showed continued progression. A needle biopsy was performed to examine whether the tumor remained HER-positive. The genetic analysis and FISH testing on FFPE sections confirmed the amplification and overexpression of HER2 with minimal genetic changes from the prior biopsy in November, 2012. The patient was treated with trastuzumab, lapatinib, vinorelbine, and high dose tamoxifen for a 4 week course, but symptoms of pelvic pain, nausea, and abdominal bloating worsened, and carboplatin was substituted for the vinorelbine and tamoxifen based on results in a mouse xenograft study. The patient continues today on this regimen of carboplatin, trastuzumab and lapatinib. A CT\PET scan on September 3, shows progression of disease.

Whole genome sequencing and quantitative proteomic analysis were performed in the patient after relapse following treatment with carboplatin/gemcitabine, vinorelbine/tamoxifen/gefitinib, and non-response to further rounds of carboplatin/gemcitabine. Analysis of the whole genomic sequence showed the patient's tumor sample to include a significant number of reads mapping to HPV type 18, in addition to containing a high number of somatic mutations, several somatic rearrangements and loss of heterozygosity of chromosome 22 (data not shown). Mutations in ERBB2, CDH1, CLTCL1, and PTPRK were noted, all of which are commonly found in breast cancer. Analysis of her tumor genome revealed evidence of HPV-18 in her tumor sample, including genomic integration resulting in significant amplification of the ERBB2 gene. Proteomic analysis of formalin fixed tissue by mass spectroscopy validated and quantitated overexpression of HER2 protein in the patient's tumor cells resulting from the ERBB2 amplification. Overexpression at the levels seen in this patient correlate with FISH-positive amplification and clinical efficacy of trastuzumab.

Based on these comprehensive omic (genomic plus proteomic) findings, trastuzamab, (a therapy approved for breast and gastric cancer), was administered, with a remarkable response stabilizing disease in the patient for months, after previous relapses after over four lines of chemotherapy. Subsequent CT/PET scan confirmed the significant shrinkage of her tumor in response to trastuzumab. Thus, and viewed from a different perspective, it should be appreciated that the molecular signature of a cancer patient may be independent of the anatomical tumor type, which necessitates use of whole genome sequencing to determine chromosomal rearrangements that may be directly tied to survival outcome.

Methods: Whole genome sequencing was performed by Illumina Clinical Services Laboratory on biopsied tissue and matched normal producing approximately 2.5 billion reads resulting in sequencing depths of 45.85× and 30.69× respectively. All reads were aligned using the BWA (Burrows-Wheeler Aligner, see e.g., http://bio-bwa.sourceforge.net/) to a modified UCSC human reference HG19 that was modified to include all known viral sequences available in NCBI as of Mar. 5, 2013, where each of the viral sequences was treated in the reference file as a separate chromosome. The Five3 Genomics sequence processing platform was used to produce copy-number estimates, somatic variants, and rearrangements as described, for example, in WO2013/074058A1, WO2011/149534A2, and WO2013/086424A1, all of which are incorporated by reference herein.

Results: Genomic sequence analysis showed the patient's tumor sample to include a significant number of reads mapping to HPV type 18, in addition to containing 48 somatic mutations, 4 somatic rearrangements and loss of heterozygosity (LOH) of chromosome 22; two of these alterations (ERBB2 and CDH1) in addition to the HPV-18 + status had known associations with cancer (as described in the Sanger Cancer Gene Census) and thus were deemed relevant to the patient's cervical cancer diagnosis. A missense mutation in XAB2 was also identified as clinically relevant after a literature review unveiled its role in genome stability and sensitivity to PARP inhibitors. In addition, chromosome 22 experienced a loss of heterozygosity (LOH) event that included the deletion of a single copy of known cancer genes CLTCL1, SMARCB1, EP300 and NF2.

ERBB2 is a proto-oncogene receptor tyrosine kinase which codes for the protein ErbB2 growth factor receptor (HER-2/neu); HER2 binds to other EGF receptors to form a heterodimer which stabilizes ligand binding and promotes kinase mediated downstream pathways, some of which promote cell growth and inhibit apoptosis. Over-expression of HER2 is known to occur in breast, ovarian, stomach, and aggressive forms of uterine cancer and is usually associated with poor survival rates. In this patient ERBB2 appears to be both amplified and flanked by rearrangements that map directly to the HPV 18 sequence as is shown in FIG. 1. More specifically, FIG. 1 depicts a graphical representation of a portion of chromosome 17 of the patient at about position 37.85 mb and downstream regions as indicated at the top of the graph. The arrows and boxes within arrow near the bottom of the graph schematically indicate genes, with the ERBB2 gene shown in full, with the boxes representing the exons of the respective genes. The box above the genes shows in line graph form the copy number of the sequences for the particular region. As is readily apparent form the line graph, a large section of the human sequences on chromosome 17 are amplified at substantially the same copy number, with a small gap in between. The half-circle icon above the gap indicates a genomic rearrangement that connects the respective ends of the amplified sequence facing each other, while the quarter circle icons in the segment above indicate a connection of the human sequence of chr 17 to another sequence outside of chr17. In this case, the other sequence is NC_001357.1, which is HPV-18. Therefore, it should be readily apparent that a genomic rearrangement o chr.17 and HPV-18 sequences has occurred. For ease of reference, human contiguous sequences from chr. 17 are schematically depicted as blocks labeled as h1, h2, h3, and h3.

Figure 2:
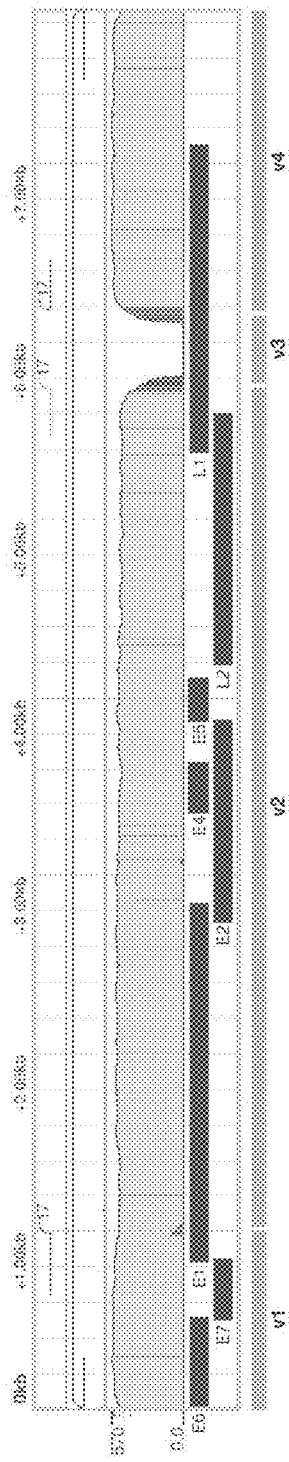
FIG. 2 is a detail view of an exemplary result of chimeric reference DNA analysis in which integration and co-amplification of human DNA (17) into the genome of HPV-18 is depicted. Only the viral genome of an HPV-18 virus is depicted.

FIG. 2 illustrates the results from the same patient when looking at the HPV-18 viral genome sequence in the chimeric reference nucleic acid sequence (only the 'chromosome' for HPV-18 is shown here). Here, amplification is again indicated as line graph while the corresponding viral genes E1, E2, E4, E5-7, L1 and L2 are indicated as boxes below the line graph. As can be seen from the stretched semicircle above the line graph, reads are present that connect the terminal ends of the viral genome, which is indicative of a circular genome. As is also readily apparent, from the quarter circles above the semi-circle, reads exist that connect the HPV-18 sequence with sequences in the human chr.17. Notably, a portion of the viral L1 gene is deleted in HPV-18. Again, for ease of reference, contiguous viral sequences are labeled as v1, v2, v3, and v4.

Figure 3:
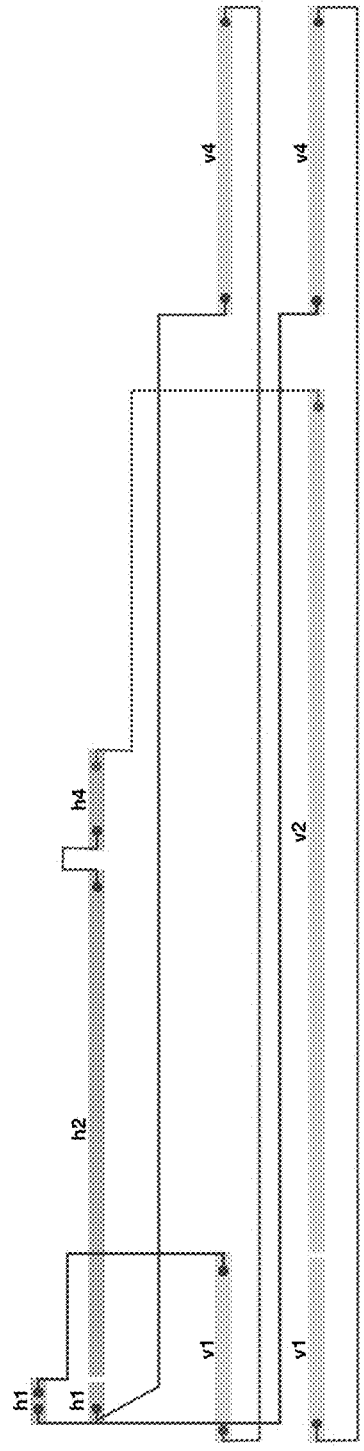
FIG. 3 is an exemplary graphical representation of a circular solution for genomic rearrangement between co-amplified HPV-18 sequences (v1, v2, v4) and human sequences (h1, h2, h4) shown in FIGS. 1 and 2.
Figure 4:
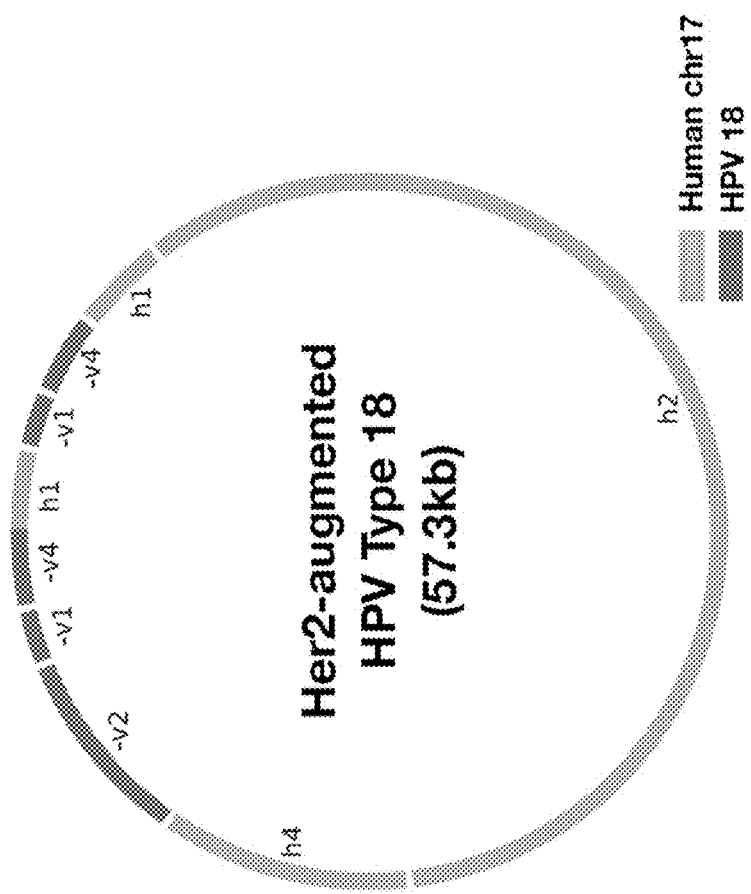
FIG. 4 is an exemplary graphical plot for the circular solution of FIG. 3 shown as a chimeric recombinant viral genome for HPV-18.

Taken together, it should thus be readily apparent that portions of the viral HPV-18 genome and the human chr.17 share contiguous reads, which are representative of a mutual genomic rearrangement in which a portion of the HPV-18 genome is integrated into the human genome, but also in which a portion of the human genome is integrated into the viral genome. FIG. 3 illustrates a graphical arrangement that is consistent with the information that can be seen in both FIGS. 1 and 2. As can be seen from FIG. 3, the left end of amplified human segment h1 connects to the left end of amplified viral segment v4 (see also first quarter-circle on the left in FIG. 1 and last quarter -circle on the right in FIG. 2), the right end of which then connects to the left end of amplified viral segment v1 (see also ends of stretched semi-circle in FIG. 2). Analysis of the points of rearrangement can be performed to arrive at a circular solution as is schematically illustrated in FIG. 4, showing a circular HPV-18 viral genome that includes large portions of ERBB2 (note that lack of h3 does not affect any exon in ERBB2).

The amplification appears to have resulted in approximately 18 total copies with a minority allele count of 1. This implies that the amplification event involved only one of the two alleles of ERBB2. In a small percentage of reads, there appears to be a rearrangement that effectively deletes exon 16, although the depth of this indicates it was likely a late event. The functional implications of this late rearrangement are unclear Immunohistochemistry of biopsied tissue from this patient confirmed the overexpression of HER2 in her tumor cells.

This patient was found to be HPV-18+, both through the discovery of signature genome from HPV-18 in the patient's genome as well as by fluorescence in situ hybridization (FISH) of biopsied samples. The data (see FIGS. 1-4 depicting patient's chromosome 17q12 with significant copy number alterations, and HPV type 18 with L1 deletion) clearly show unambiguous rearrangements from the HPV-18 genome to the region flanking HER2 on chromosome 17, with copy-number directly supporting equal number of copies of HER2 and HPV-18. This implies that either the HPV genome integrated HER2 directly into its sequence in place of L1 (a capsid protein), or the integration of HPV-18 into the patient's genome enabled tandem duplication of the sequence including HER2 to be copied multiple times into chromosome 17. Regardless of manner of integration, it should be appreciated that the amplification of ERBB2 strongly suggested that the finding of overexpressed Her2 in the patient was due to the genomic integration and co-amplification of the ERBB2 gene and as such presented a new treatment target that was observed effective by administration of an Her2 inhibitor.

The patient presented with cervical cancer, however, the sequencing based test points towards a unique presentation-mutations which more commonly are found in breast cancers; in this patient we see ERBB2, CDH1, CLTCL1, all of which can be found in breast cancers. Also of note is the patient's HPV-18+ status, with the loss of its L1 capsid gene, which is indicative of tumor progression.

HPV-16 and 18 are considered to be the highest-risk HPV strains. As can also be seen from FIG. 4, the HPV capsid protein known as L1, which was found to be deleted in this patient, often is present in the initial infection and production stages, but is deleted or not expressed during premalignant transformation. Reduction of L1 expression has been associated with the progression of cervical intraepithelial lesions to invasive cervical cancer. The two additional HPV proteins of note in cancer are E6 and E7, which bind and inactivate the tumor suppressors P53 and pRb, respectively (WHO/ICO information centre on Human Papilloma Virus (HPV) and Cervical Cancer, www.who.int/hpvcentre).

The presence of the HPV-18 genome minus its L1 capsid gene and the deletion of the CLTCL1 clathrin gene are potentially interesting coincidental discoveries. HPV L1 mediates clathrin-dependent cellular entry by binding heparin sulfate proteoglycans on the surface of epithelial cells. Clathrin-independent endocytosis may be mediated by the minor capsid protein L2 via annexin A2. CLTCL1 is a necessary component of clathrin-mediated infectivity by dengue virus and human enterovirus 71.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C..., and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A computer-implemented method comprising:
providing an access to a computer having an analysis engine;
obtaining, by the analysis engine, a whole genome nucleic acid sequence from a virus-associated tumor and a chimeric reference nucleic acid sequence file;
wherein the chimeric reference nucleic acid sequence file has a chromosomal structure format, wherein the chimeric reference nucleic acid sequence file comprises a chimeric reference nucleic acid sequence that is generated, by an editing engine, by merging at least one viral genome nucleic acid sequence and a mammalian genome nucleic acid sequence;
aligning the chimeric reference nucleic acid sequence and the nucleic acid sequence from the virus-associated tumor, using incremental synchronized alignment, by the analysis engine, to identify an integration of at least some of the viral nucleic acid sequence in the chimeric reference nucleic acid sequence with an allele in the nucleic acid sequence from the virus-associated tumor;
quantifying a copy number of the allele, by the analysis engine, from an alignment of the chimeric reference nucleic acid sequence and the nucleic acid sequence from a virus-associated tumor, to identify co-amplification of the allele and the at least some of the viral nucleic acid sequence; and
generating a treatment recommendation record recommending treating the virus-associated tumor by using a drug targeting the allele, once a magnitude of co-amplification reaches a threshold value.

2. The method of claim 1 wherein the nucleic acid sequence from the virus-associated tumor comprises at least nucleic acid sequences of one chromosome of the virus-associated tumor.

3. The method of claim 1 wherein the nucleic acid sequence from the virus-associated tumor comprises at least 50% of an exome of the virus-associated tumor.

4. The method of claim 1 wherein the nucleic acid sequence from the virus-associated tumor comprises at least 50% of an entire genome of the virus-associated tumor.

5. The method of claim 1 wherein the virus-associated tumor is associated with a virus selected from the group consisting of HTLV-1 (Human T-Cell Leukemia Virus), an HPV virus (Human Papillomavirus), HHV-8 (Human Herpes Virus 8), EBV (Epstein-Barr Virus), HBV (Hepatitis B Virus), HCV (Hepatitis C Virus), SV40 (Simian Vacuolating Virus 40), BKV (BK virus), JCV (JC virus), a HERV (human endogenous retrovirus), HMTV (human mammary tumor virus), KSHV (Kaposi's Sarcoma-Associated Herpesvirus), and TTV (Torque teno virus).

6. The method of claim 1 wherein the virus-associated tumor is associated with an HPV virus of type 16, 18, 31, 33, 35, 39, 45, 51, 52, 56, 58, 59, 68, 69, 73, or 82.

7. The method of claim 1 wherein the chimeric reference nucleic acid sequence comprises a plurality of viral nucleic acid sequences from a plurality of distinct viruses.

8. The method of claim 1 wherein the mammalian nucleic acid sequence in the chimeric reference nucleic acid sequence is a matched normal mammalian nucleic acid sequence.

9. The method of claim 1 wherein the nucleic acid sequence from the virus-associated tumor and the chimeric reference nucleic acid sequence are in BAM, SAM, FASTA, or FASTA index format.

10. The method of claim 1 wherein the allele in the nucleic acid sequence from the virus-associated tumor comprises an oncogene.

11. The method of claim 1 wherein the step of identifying integration comprises identification of a location of integration, by incremental synchronous alignment between the nucleic acid sequence from a virus-associated tumor and the chimeric reference nucleic acid sequence.

12. The method of claim 1 further comprising a step of determining a solution for a genomic arrangement comprising the co-amplified sequences, by identifying a connection between one end of the oncogene allele and one end of the at least some of the viral nucleic acid sequence.

13. The method of claim 1 wherein the threshold value is greater than 10 amplifications.

14. A method comprising:
providing an access to a computer having an analysis engine;
obtaining, by the analysis engine, a whole genome nucleic acid sequence from a cervical tumor of a patient and a chimeric reference nucleic acid sequence file;
wherein the chimeric reference nucleic acid sequence file has a chromosomal structure format, wherein the chimeric reference nucleic acid sequence file comprises matched normal nucleic acid sequence from the patient and a viral nucleic acid sequence of an HPV virus;
aligning the chimeric reference nucleic acid sequence and the nucleic acid sequence from the cervical tumor, using incremental synchronized alignment, by the analysis engine, to identify an integration of at least some of the viral nucleic acid sequence in the chimeric reference nucleic acid sequence with an allele of an oncogene in the nucleic acid sequence from the cervical tumor;
quantifying a copy number of the allele, by the analysis engine, from an alignment of the chimeric reference nucleic acid sequence and the nucleic acid sequence from the cervical tumor, to identify co-amplification of the allele and the at least some of the viral nucleic acid sequence; and
generating a treatment recommendation record recommending treating the virus-associated tumor by using a drug targeting the allele, once a magnitude of co-amplification reaches a threshold value.

15. The method of claim 14 wherein the nucleic acid sequence from the cervical tumor comprises at least nucleic acid sequences of one chromosome of the cervical tumor.

16. The method of claim 14 wherein the nucleic acid sequence from the cervical tumor comprises at least 50% of an exome of the cervical tumor.

17. The method of claim 14 wherein the nucleic acid sequence from the cervical tumor comprises at least 50% of an entire genome of the cervical tumor.

18. The method of claim 14 wherein the chimeric reference nucleic acid sequence comprises at least two nucleic acid sequences of an HPV virus of type 16, 18, 31, 33, 35, 39, 45, 51, 52, 56, 58, 59, 68, 69, 73, or 82.

19. The method of claim 18 wherein the at least two nucleic acid sequences of the HPV virus cover the entire genome of the HPV virus.

20. The method of claim 14 wherein the oncogene is a gene encoding a growth factor receptor.

21. The method of claim 20 wherein the oncogene is ERBB2.

22. The method of claim 14 wherein the allele is a homozygous allele.

23. The method of claim 14 further comprising a step of determining a solution for a genomic arrangement comprising the co-amplified sequences.

24. The method of claim 23 wherein the genomic arrangement is a circular solution or a tandem duplication.

25. The method of claim 14 wherein the treatment recommendation record comprises administration of a drug targeting the oncogene.

* * * * *